United States Patent
Chen et al.

(10) Patent No.: US 11,249,001 B2
(45) Date of Patent: Feb. 15, 2022

(54) DETERMINATION OF SCANNING LOOPS OF CAPILLARY PRESSURE AND RELATIVE PERMEABILITY CURVES AND WETTABILITY DISTRIBUTION OF ROCK SAMPLES

(71) Applicant: Saudi Arabian Oil Company, Dhahran (SA)

(72) Inventors: Quan Chen, Al Khobar (SA); Sultan Muhammad Al Enezi, Dammam (SA); Ali Abdallah Al-Yousef, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 398 days.

(21) Appl. No.: 16/420,923

(22) Filed: May 23, 2019

(65) Prior Publication Data
US 2020/0371011 A1    Nov. 26, 2020

(51) Int. Cl.
*G01N 15/08* (2006.01)
*G01N 33/24* (2006.01)

(52) U.S. Cl.
CPC ....... *G01N 15/0826* (2013.01); *G01N 33/241* (2013.01); *G01N 33/246* (2013.01)

(58) Field of Classification Search
CPC . G01N 33/241; G01N 33/246; G01N 15/0826
See application file for complete search history.

(56) References Cited

U.S. PATENT DOCUMENTS 5,679,885 A    10/1997    Lenorman et al.
6,178,807 B1    1/2001    Baldwin et al.
(Continued)

FOREIGN PATENT DOCUMENTS

CN    112098449 A    * 12/2020
EP    2341372    7/2011

OTHER PUBLICATIONS

Dernaika et al. "Variations in Bounding and Scanning Relative Permeability Curves with Different Carbonate Rock Types," SPE-162265 (Year: 2012).*
(Continued)

*Primary Examiner* — John Fitzgerald
(74) *Attorney, Agent, or Firm* — Fish & Richardson P.C.

(57) ABSTRACT

A primary drainage process, a core aging process, a spontaneous water imbibition process, a forced water imbibition process, a spontaneous hydrocarbon imbibition process, and a secondary drainage process is conducted on a rock sample. For each of the primary drainage process, the spontaneous water imbibition process, the forced water imbibition process, the spontaneous hydrocarbon imbibition process, and the secondary drainage process, a pressure distribution and a fluid saturation distribution are measured across multiple locations along the rock sample. For each of the locations, the pressure distribution and the fluid saturation distribution are combined to produce a capillary pressure bounding curve and scanning loop for the rock sample, and a relative permeability bounding curve and scanning loop are determined at least based on the measured fluid saturation and pressure distributions at the respective location. A wettability distribution along the rock sample is determined based on the bounding curves and scanning loops.

20 Claims, 7 Drawing Sheets

(56) References Cited

U.S. PATENT DOCUMENTS

| | | | |
|---|---|---|---|
| 8,042,382 B1 | 10/2011 | Fleury et al. | |
| 10,287,486 B2 | 5/2019 | Ayirala et al. | |
| 10,422,733 B2 | 9/2019 | Yang et al. | |
| 10,723,937 B2 | 7/2020 | Ayirala et al. | |
| 10,895,543 B2* | 1/2021 | Chen | G01R 33/50 |
| 2011/0271751 A1* | 11/2011 | Brooks | G01V 11/002 73/152.07 |
| 2012/0241149 A1 | 9/2012 | Chen et al. | |
| 2013/0261979 A1 | 10/2013 | Al-muthana et al. | |
| 2013/0325348 A1 | 12/2013 | Valori et al. | |
| 2014/0340082 A1 | 11/2014 | Yang et al. | |
| 2015/0104078 A1 | 4/2015 | Varslot et al. | |
| 2015/0219789 A1 | 8/2015 | Pairoys | |
| 2016/0290942 A1* | 10/2016 | Wang | G01N 24/081 |
| 2016/0334346 A1 | 11/2016 | Minh et al. | |
| 2017/0015893 A1 | 1/2017 | Al-Yousef et al. | |
| 2019/0346385 A1 | 11/2019 | Reiderman et al. | |
| 2019/0368994 A1 | 12/2019 | Al Readean et al. | |
| 2020/0371051 A1 | 11/2020 | Chen et al. | |

OTHER PUBLICATIONS

Johannesen et al., "Evaluation of wettability distributions in experimentally aged core," SCA2008-17, presented at the International Symposium of the Society of Core Analysts, Abu Dhabi, UAE, Oct. 29-Nov. 2, 2008, 12 pages.

Liang et al., "Wettability characterization of low-permeability reservoirs using nuclear magnetic resonance: an experimental study," Journal of Petroleum Science and Engineering, Mar. 2019, 178:121-132.

Mitchell et al., "Magnetic resonance imaging in laboratory petrophysical core analysis," Physics Reports, North Holland, Amsterdam, Jan. 2013, 526(3):165-225.

PCT International Search Report and Written Opinion in International Appln. No. PCT/US2020/034214, dated Sep. 2, 2020, 17 pages.

Chen et al., "A mechanism study of co-current and counter-current imbibition using new magnetic resonance techniques," SCA2005-38, 2005, 16 pages.

Fu et al., "Modeling and simulation of transition zones in tight carbonate reservoirs by incorporation of improved rock typing and hysteresis models," Journal of Petroleum Exploration and Production Technology vol. 8, 2018, 18 pages.

OnePetro [online], available on or before Apr. 1, 2007, retrieved on Nov. 2, 2018, URL <https://www.onepetro.org/>, 2 pages.

Perrin et al., "Core-scale experimental study of relative permeability properties of CO2 and brine in reservoir rocks," Energy Procedia vol. 1, 2009, 8 pages.

Shi et al., "Capillary pressure and relative permeability correlations for transition zones of carbonate reservoirs," Journal of Petroleum Exploration Production and Technology, vol. 8, 2018, 18 pages.

Siqveland et al., "Aging time control by NMR relaxation," 7th International Symposium on Reservoir Wettability, Tasmania, Australia, Jan. 1991, 10 pages.

Spearing et al., "Transition Zone Behaviour: The Measurement of Bounding and Scanning Relative Permeability and Capillary Pressure Curves at Reservoir Conditions for a Giant Carbonate Reservoir," presented at the Abu Dhabi International petroleum Exhibition and Conference, Nov. 10-13, 2014, 14 pages.

Williams et al., "Application of Magnetic resonance imaging in special core analysis studies," Reviewed Proceeding 1st Soc. Core Analysts European Core Analysis Symp. Gordon and Breach London, 1990, 30 pages.

PCT International Search Report and Written Opinion in International Appln. No. PCT/US2020/034211, dated Aug. 17, 2020, 15 pages.

* cited by examiner

DETERMINATION OF SCANNING LOOPS OF CAPILLARY PRESSURE AND RELATIVE PERMEABILITY CURVES AND WETTABILITY DISTRIBUTION OF ROCK SAMPLES

TECHNICAL FIELD

This disclosure generally relates to methods and systems for testing rock samples.

BACKGROUND

For multiphase fluid flow, the relative permeability, capillary pressure, and wettability are dynamic parameters that govern the multiphase flow behavior in porous media. The study of such parameters can be valuable in evaluating and predicting hydrocarbon recovery from hydrocarbon-containing reservoirs.

The characteristics of capillary pressure, relative permeability, and wettability distribution in such reservoirs, however, can be complex. Furthermore, both capillary pressure and relative permeability can depend not only on fluid saturation but also on fluid saturation path and history, which is a phenomenon that is sometimes referred to as hysteresis. Several hydrocarbon recovery processes involve changing directions of fluid saturation paths, such as water alternating gas (WAG) enhanced oil recovery (EOR) processes and cyclic injection processes, such as huff and puff operations in heavy oil recovery.

SUMMARY

The present disclosure describes techniques that can be used for determining scanning loops of capillary pressure and relative permeability curves and wettability distribution of a rock sample. The subject matter described in this specification can be implemented in particular implementations, so as to realize one or more of the following advantages. First, scanning loops of capillary pressure, relative permeability curves, wettability distribution, and initial-residual correlations at reservoir conditions can be obtained from performing one set of tests on a single rock sample. Second, an initial water saturation distribution conditions (representative of an oil-water transition zone of a reservoir) can be maintained during the core aging process, which can prove to be difficult with conventional methods. For example, the wettability distribution that is representative of the oil-water transition zone of a reservoir can be restored after a core aging process. Third, all of the aforementioned values can be determined with a single rock sample and one set of tests, which can prove to be quicker, more efficient, and more economical in comparison to running multiple tests across multiple rock samples. Furthermore, because the entire set of tests is performed on a single rock sample, the comparison of obtained data can be more straightforward and reliable than comparing data sets of different rock samples. The scanning loops of capillary pressure and relative permeability curves and the wettability distribution can be used in evaluating and predicting hydrocarbon recovery from an oil-water transition zone of a reservoir, where initial oil and water saturation and wettability are dependent on the height greater than the free water level.

Certain aspects of the subject matter described can be implemented as a method. A primary drainage process, a core aging process, a spontaneous water imbibition process, a forced water imbibition process, a spontaneous hydrocarbon imbibition process, and a secondary drainage process is conducted on a rock sample. For each of the primary drainage process, the spontaneous water imbibition process, the forced water imbibition process, the spontaneous hydrocarbon imbibition process, and the secondary drainage process, a pressure distribution and a fluid saturation distribution are measured across multiple locations along a longitudinal length of the rock sample. For each of the locations along the longitudinal length of the rock sample, the pressure distribution and the fluid saturation distribution are combined to produce a capillary pressure bounding curve and scanning loop for the rock sample at the respective location. For each of the locations along the longitudinal length of the rock sample, a relative permeability bounding curve and scanning loop are determined at least based on the measured fluid saturation distribution and pressure distribution at the respective location. A wettability distribution along the longitudinal length of the rock sample is determined based on the capillary pressure bounding curves and scanning loops.

This, and other aspects, can include one or more of the following features.

The rock sample can be saturated with a water stream. An imaging machine can be calibrated using the rock sample saturated with the water stream. A permeability distribution across the locations along the longitudinal length of the rock sample can be determined based on the measured pressure distribution. The permeability distribution across the locations along the longitudinal length of the rock sample can be determined using Darcy's Law.

A cleaning process can be conducted on the rock sample. The cleaning process can include flowing toluene through the rock sample, flowing methanol through the rock sample, and repeating and alternating between toluene and methanol until an effluent from the rock sample is visually clear. Once the effluent from the rock sample is visually clear, if the last fluid flowed through the rock sample was methanol, toluene can be flowed through the rock sample once more.

The rock sample can be saturated with a hydrocarbon stream. An imaging machine can be calibrated using the rock sample saturated with the hydrocarbon stream.

Each of the primary drainage process and the core aging process can include flowing a hydrocarbon stream into a first end of the rock sample at a first hydrocarbon flow rate, and while flowing the hydrocarbon stream, flowing a water stream across a second end of the rock sample at a first water flow rate.

The spontaneous water imbibition process can include flowing the water stream across the second end of the rock sample at the first water flow rate, and while flowing the water stream, flowing the hydrocarbon stream into the first end of the rock sample at a second hydrocarbon flow rate.

The spontaneous water imbibition process can include, while flowing the water stream and after flowing the hydrocarbon stream at the second hydrocarbon flow rate, decreasing the flow of the hydrocarbon stream into the first end of the rock sample.

The spontaneous water imbibition process can include, while flowing the water stream, flowing the hydrocarbon stream across the first end of the rock sample.

The forced water imbibition process can include flowing the hydrocarbon stream across the first end of the rock sample at a third hydrocarbon flow rate, and while flowing the hydrocarbon stream, flowing the water stream into the second end of the rock sample at a second water flow rate.

The forced water imbibition process can include, while flowing the hydrocarbon stream and after flowing the water stream at the second water flow rate, increasing the flow of the water stream into the second end of the rock sample.

The spontaneous hydrocarbon imbibition process can include flowing the hydrocarbon stream across the first end of the rock sample at the third hydrocarbon flow rate, and while flowing the hydrocarbon stream, flowing the water stream into the second end of the rock sample at a third water flow rate.

The spontaneous hydrocarbon imbibition process can include, while flowing the hydrocarbon stream and after flowing the water stream at the third water flow rate, decreasing the flow of the water stream into the second end of the rock sample.

The spontaneous hydrocarbon imbibition process can include, while flowing the hydrocarbon stream, flowing the water stream across the second end of the rock sample.

The secondary drainage process can include flowing the water stream across the second end of the rock sample at the first water flow rate, and while flowing the water stream, flowing the hydrocarbon stream into the first end of the rock sample at a fourth hydrocarbon flow rate.

The secondary drainage process can include, while flowing the water stream and after flowing the hydrocarbon stream at the fourth hydrocarbon flow rate, increasing the flow of the hydrocarbon stream into the first end of the rock sample.

A correlation between an initial hydrocarbon saturation and a residual hydrocarbon saturation can be determined based on the measured fluid saturation distributions across the plurality of locations along the longitudinal length of the rock sample. The correlation can be determined based on measurements of an initial hydrocarbon saturation distribution and a residual hydrocarbon saturation distribution.

For each of the locations (x) along the longitudinal length of the rock sample, a relative permeability of a water phase ($K_{rw}$) can be determined to be:

$$K_{rw}(x) = -\frac{V_w \mu_w}{K}\left(\frac{dP_w(x)}{dx}\right)^{-1},$$

where K is absolute permeability, $V_w$ is velocity of the water phase flowing through the rock sample, $\mu_w$ is dynamic viscosity of the water phase, $dP_w(x)$ is pressure drop of the water phase, and dx is length over which the pressure drop is taking place.

For each of the locations (x) along the longitudinal length of the rock sample, the relative permeability of the water phase ($K_{rw}$) can be determined to be:

$$K_{rw}(x) = \frac{x \mu_w}{K} \frac{dV_w}{dP_w(x, V_w)}.$$

For each of the locations (x) along the longitudinal length of the rock sample, a relative permeability of a hydrocarbon phase ($K_{ro}$) can be determined to be:

$$K_{ro}(x) = -\frac{V_o \mu_o}{K}\left(\frac{dP_o(x)}{dx}\right)^{-1},$$

where K is absolute permeability, $V_o$ is velocity of the hydrocarbon phase flowing through the rock sample, $\mu_o$ is dynamic viscosity of the hydrocarbon phase, $dP_o(x)$ is pressure drop of the hydrocarbon phase, and dx is length over which the pressure drop is taking place.

For each of the locations (x) along the longitudinal length (L) of the rock sample, the relative permeability of the hydrocarbon phase ($K_{ro}$) can be determined to be:

$$K_{ro}(x) = \frac{(L-x)\mu_o}{K} \frac{dV_o}{dP_o(x, V_o)}.$$

Certain aspects of the subject matter described can be implemented as a system configured to implement any one of the methods described above.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DETAILED DESCRIPTION

This disclosure describes determining scanning loops of capillary pressure and relative permeability curves and wettability distribution of a rock sample, for example, obtained from a subterranean formation. Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

Figure 1:
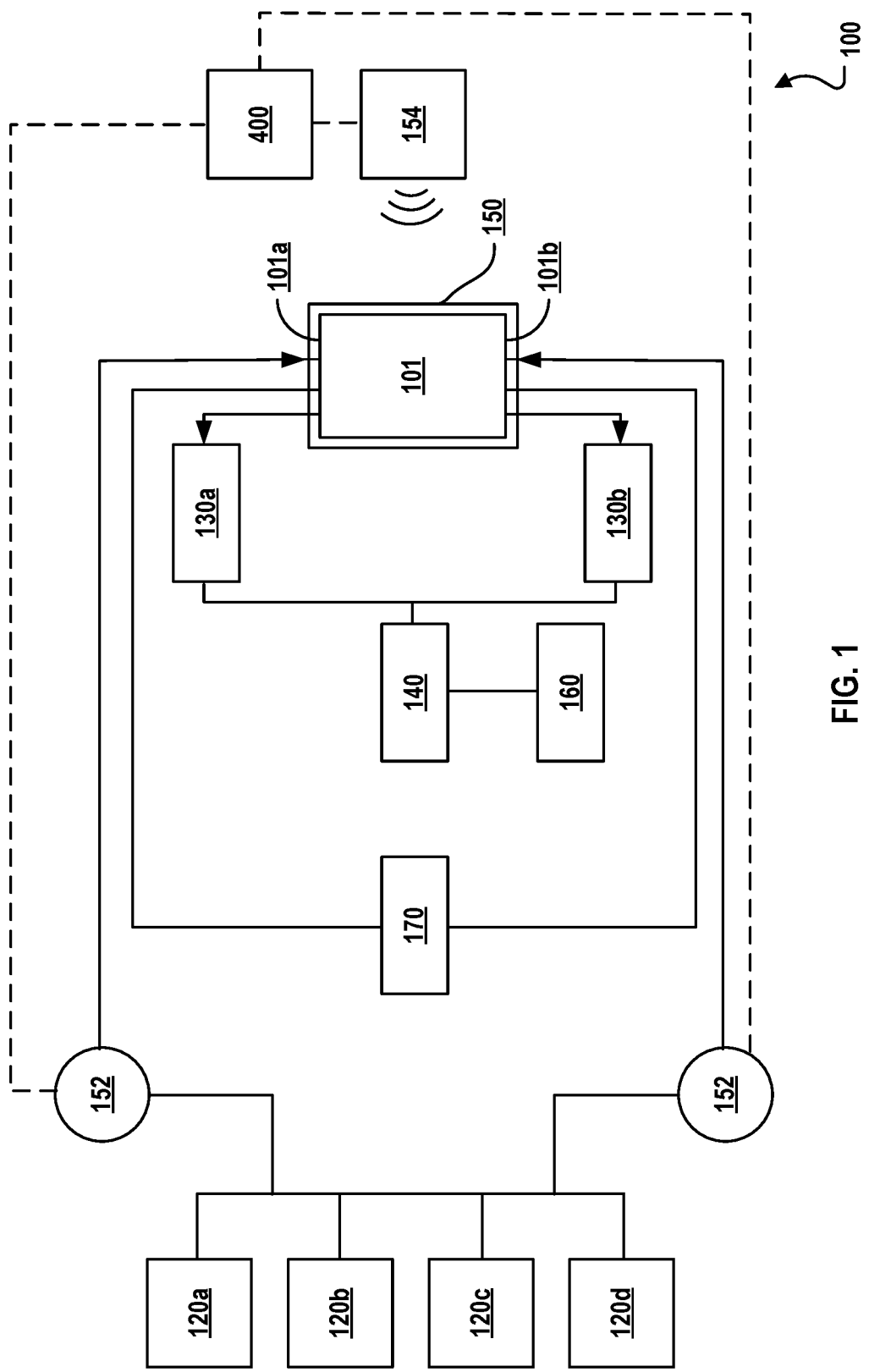
FIG. 1 is a schematic diagram of an example system that can be used to determine capillary pressure and relative permeability bounding curves and scanning loops and wettability distribution of a rock sample.

FIG. 1 is an example system 100 that can be used to determine scanning loops of capillary pressure and relative permeability curves and wettability distribution of a rock sample 101. The system 100 can include a rock sample holder 150, a hydrocarbon stream source 120a, a water stream source 120b, a toluene stream source 120c, a methanol stream source 120d, flow control valves 130a and 130b, a backpressure regulator 140, injection pumps 152, an imaging machine 154 for in-situ fluid saturation monitoring, an effluent collection and measurement system 160, and a differential pressure measurement system 170. The sample holder 150 is made of a material that does not interfere with image capture by the imaging machine 154. For example, the sample holder 150 is made of carbon fiber composite. The rock sample 101 can be held by the sample holder 150, for example, in a vertical orientation or in a horizontal orientation. The system 100 can include a confining pressure system (not shown) for maintaining a constant hydrostatic overburden pressure for the sample holder 150. The flow control valves 130a and 130b can be used to control fluid flow to and from the rock sample 101. For example, control valve 130a can be designated for controlling fluid flow into and out of the first end 101a of the rock sample 101, and control valve 130b can be designated for controlling fluid flow into and out of the second end 101b of the rock sample 101. The backpressure regulator 140 can be used to control backpressure in the system 100. Backpressure is the pressure downstream of the rock sample 101. For example, the backpressure regulator 140 can be used to maintain a constant backpressure in the system 100. The effluent collection and measurement system 160 can be used to collect and measure the effluent from the rock sample 101. The differential pressure measurement system 170 can be used to measure the differential pressure across the rock sample 101. The differential pressure measurement system 170 can include multiple differential pressure transducers connected to pressure taps (not shown) positioned along a longitudinal length of the rock sample 101 so that pressure at the respective locations along the longitudinal length of the rock sample 101 can be measured. The various differential pressure transducers can be connected to each end (101a and 101b) of the rock sample 101. In some implementations, the differential pressure transducers can have various differential pressure ranges.

In some implementations, the injection pumps 152 can be connected to each of the hydrocarbon stream source 120a, the water stream source 120b, the toluene stream source 120c, and the methanol stream source 120d. In some implementations, the system 100 includes additional injection pumps 152, and each of the injection pumps 152 are designated for one of the sources 120a, 120b, 120c, or 120d. In some implementations, each of the injection pumps 152 is designated for flowing fluid to one of the ends (101a or 101b) of the rock sample 101. For example, one injection pump 152 can be designated for flowing fluid to a first end 101a of the rock sample 101, and the other injection pump 152 can be designated for flowing fluid to a second end 101b of the rock sample 101. In such implementations, each of the injection pumps 152 can be connected to each of the sources 120a, 120b, 120c, and 120d. In some implementations, after fluid phase separation, effluent from the rock sample 101 is recycled to one of the sources 120a or 120b. In some implementations, effluent from the rock sample 101 is collected and subsequently measured using the effluent collection and measurement system 160. The system 100 can include a computer 400 to perform operations, such as controlling one or more of the components of the system 100 (for example, the injection pump 152 and the imaging machine 154) and performing calculations. The imaging machine 154 can be, for example, an x-ray imaging machine or a magnetic resonance imaging machine.

Figure 2:
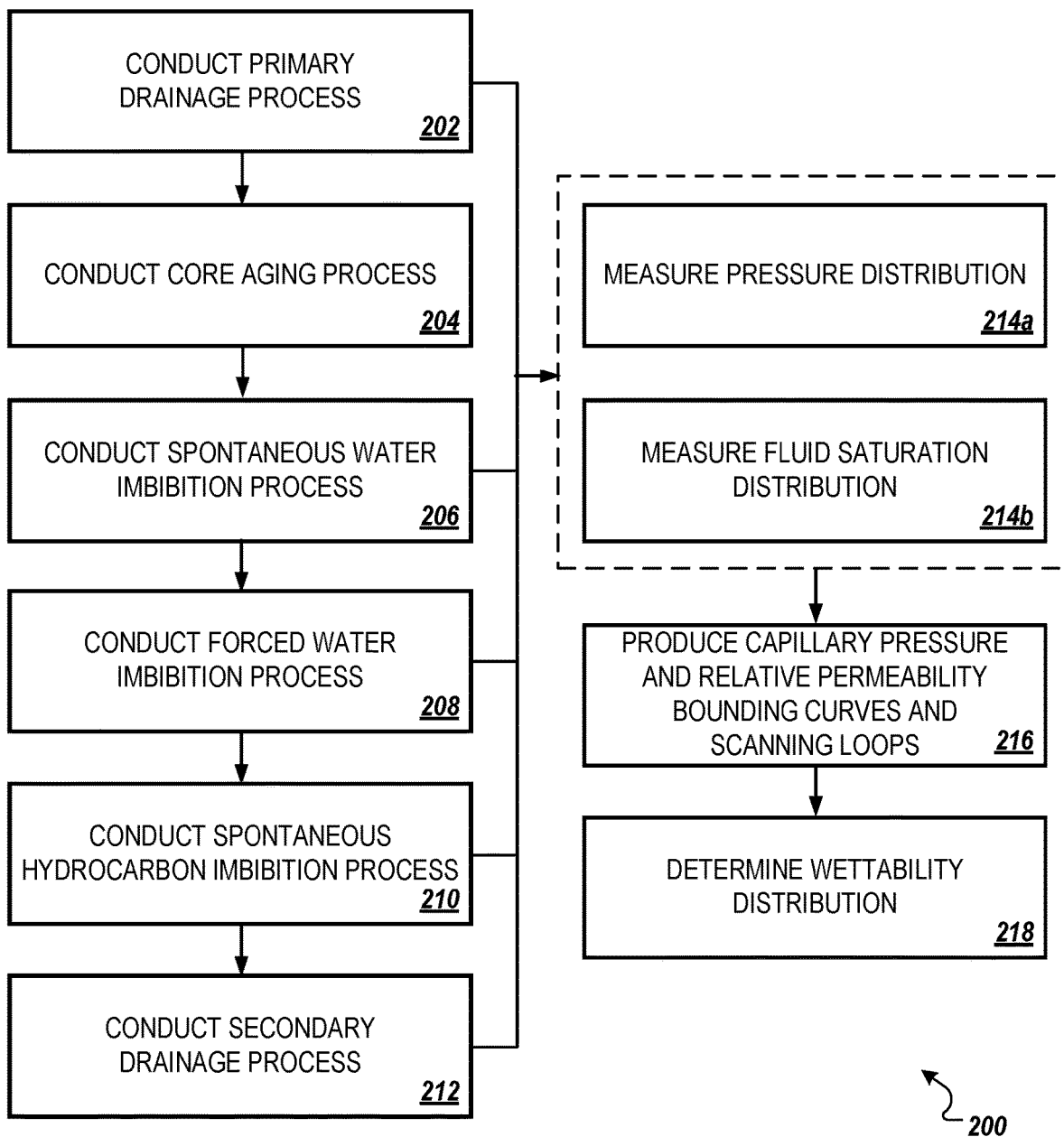
FIG. 2 is a flowchart of an example method for determining capillary pressure and relative permeability bounding curves and scanning loops and wettability distribution of a rock sample.

FIG. 2 is a flowchart of an example method 200 for determining scanning loops of capillary pressure and relative permeability curves and wettability distribution of a rock sample (such as the rock sample 101). For clarity of presentation, the description that follows generally describes method 200 in the context of the other figures in this description (for example, the method 200 can be implemented using the system 100). However, it will be understood that method 200 can be performed, for example, by any suitable system, environment, software, and hardware, or a combination of systems, environments, software, and hardware, as appropriate. In some implementations, various steps of method 200 can be run in parallel, in combination, in loops, or in any order.

At the beginning of method 200, the imaging machine 154 can be calibrated with the rock sample 101 at 100% water saturation. For example, the imaging machine 154 can be an x-ray imaging machine, and the x-ray imaging machine 154 can be calibrated with the rock sample 101 at 100% water saturation at reservoir conditions. For example, reservoir conditions can be a temperature in a range of from approximately 40 degrees Celsius (° C.) to approximately 120° C. and a pressure in a range of from approximately 1,000 pounds per square inch gauge (psig) to approximately 9,500 psig. In some implementations, the rock sample 101 is maintained at reservoir conditions throughout method 200 (for example, steps 202, 204, 206, 208, 210, 212, and the final calibration process of the imaging machine 154). The water phase can be doped so that the water phase distinguishable from the oil phase by the imaging machine 154. For example, the water stream can be doped with potassium iodide, potassium bromide, or cesium chloride. The absolute permeability (K) of the rock sample 101 can be determined by flowing water through the rock sample 101 at different flow rates and monitoring the differential pressures at various locations (x) along the longitudinal length (L) of the rock sample 101. Water can be flowed through the rock sample 101, for example, at a volumetric rate in a range of approximately 0.1 cubic centimeters per minute (cc/min) to approximately 2 cc/min. The absolute permeability (K) distribution along the longitudinal length of the rock sample 101 can be calculated by linear fitting of differential pressure distribution versus flow rate data in accordance to Darcy's Law (provided in Equation 1).

$$V = -\frac{K}{\mu}\frac{dP(x)}{dx} \quad (1)$$

where V is the velocity of fluid flow that is equal to volumetric flow rate divided by the cross-sectional area to the flow (for example, the cross sectional area of the rock sample 101), $\mu$ is the dynamic viscosity of the flowing fluid, dP(x) is the pressure drop, and dx is the length over which the pressure drop is taking place.

When two phases (for example, water and oil) are present or flowing in the rock sample 101, Darcy's Law can be generalized for each phase. Equation 2 provides Darcy's Law generalized for a water phase.

$$V_w = -\frac{KK_{rw}}{\mu_w}\frac{dP_w(x)}{dx} \quad (2)$$

where $V_w$ is velocity of water flow through the rock sample 101, $K_{rw}$ is the relative permeability of the water phase, $\mu_w$ is the dynamic viscosity of the water phase, $dP_w(x)$ is the pressure drop of the water phase, and dx is the length over which the pressure drop is taking place.

Equation 3 is a rearrangement of Equation 2, solving for the water phase relative permeability ($K_{rw}$) as a function of location (x) along the longitudinal length (L) of the rock sample 101.

$$K_{rw}(x) = -\frac{V_w \mu_w}{K}\left(\frac{dP_w(x)}{dx}\right)^{-1} \quad (3)$$

Equation 4 provides Darcy's Law generalized for an oil phase.

$$V_o = -\frac{KK_{ro}}{\mu_o}\frac{dP_o(x)}{dx} \quad (4)$$

where $V_o$ is velocity of oil flow through the rock sample 101, $K_{ro}$ is the relative permeability of the oil phase, $\mu_o$ is the dynamic viscosity of the oil phase, $dP_o(x)$ is the pressure drop of the oil phase, and dx is the length over which the pressure drop is taking place.

Equation 5 is a rearrangement of Equation 4, solving for the oil phase relative permeability ($K_{ro}$) as a function of location (x) along the longitudinal length (L) of the rock sample 101.

$$K_{ro}(x) = -\frac{V_o \mu_o}{K}\left(\frac{dP_o(x)}{dx}\right)^{-1} \quad (5)$$

Local capillary pressure ($P_c$) is defined as the equilibrium pressure difference between the oil and water phases. Equation 6 provides the local capillary pressure ($P_c$) at a location (x) along the longitudinal length (L) of the rock sample 101.

$$P_c(x) = P_o(x) - P_w(x) \quad (6)$$

For various steps of method 200, a steady-state equilibrium condition can be said to be achieved when flowing one phase through the rock sample 101 ceases to cause the other phase to be displaced from the rock sample 101 (that is, the other phase is no longer being produced as effluent from the rock sample 101). For example, in steps where the oil phase is being flowed into the first end 101a (where x=0) of the rock sample 101 while the water phase is being flowed across the second end 101b (where x=L) of the rock sample 101 (such as in steps 202, 204, 206, and 212), a steady-state equilibrium condition is achieved when water no longer flows out of the rock sample 101 ($V_w$=0). At the steady-state equilibrium condition, the water phase exhibits a zero pressure gradient (that is, $dP_w(x)/dx$=0), and Equations 4 and 6 can be combined to provide Equation 7.

$$V_o dx = -\frac{KK_{ro}(P_c(x))}{\mu_o}dP_c(x) \quad (7)$$

Equation 8 provides an integration of Equation 7 along the longitudinal length (L) of the rock sample 101 and with an outlet boundary condition of $P_c(x=L)=0$.

$$V_o(L-x) = \frac{K}{\mu_o}\int_0^{P_c(x)} K_{ro}(P_c(x))dP_c(x) \quad (8)$$

For multiple oil flow rates, the pressure of the oil phase ($P_o$) across various locations (x) along the longitudinal length (L) of the rock sample 101 is a function of the respective oil flow rate ($V_o$). At the steady-state equilibrium condition, the pressure of the water phase ($P_w$) is uniform along the longitudinal length (L) of the rock sample 101 and can be considered a reference point ($P_w$=0). Equation 9 provides a differentiation of Equation 8 with respect to $P_o(x)$.

$$(L-x)\frac{dV_o}{dP_o(x)} = \frac{KK_{ro}(P_o(x))}{\mu_o} \quad (9)$$

Equation 10 provides a rearrangement of Equation 9, solving for the oil phase relative permeability ($K_{ro}$) as a function of location (x) along the longitudinal length (L) of the rock sample 101.

$$K_{ro}(x) = \frac{(L-x)\mu_o}{K}\frac{dV_o}{dP_o(x, V_o)} \quad (10)$$

As another example, in steps where the water phase is being flowed into the second end 101b (where x=L) of the rock sample 101 while the oil phase is being flowed across the first end 101a (where x=0) of the rock sample 101 (such as in steps 208 and 210), a steady-state equilibrium condition is achieved when oil no longer flows out of the rock sample 101 ($V_o$=0). At the steady-state equilibrium condition, the oil phase exhibits a zero pressure gradient (that is, $dP_o(x)/dx$=0), and Equations 2 and 6 can be combined to provide Equation 11.

$$V_w dx = \frac{KK_{rw}(P_c(x))}{\mu_w}dP_c(x) \quad (11)$$

Equation 12 provides an integration of Equation 11 along the longitudinal length (L) of the rock sample 101 and with an outlet boundary condition of $P_c(x=0)=0$.

$$xV_w = \frac{K}{\mu_w}\int_0^{P_c(x)} K_{rw}(P_c(x))dP_c(x) \quad (12)$$

For multiple water flow rates, the pressure of the water phase ($P_w$) across various locations (x) along the longitudinal length (L) of the rock sample 101 is a function of the respective water flow rate ($V_w$). At the steady-state equilibrium condition, the pressure of the oil phase ($P_o$) is uniform along the longitudinal length (L) of the rock sample 101 and can be considered a references point ($P_o$=0). Equation 13 provides a differentiation of Equation 12 with respect to $P_w(x)$.

$$x\frac{dV_w}{dP_w(x)} = \frac{KK_{rw}(P_w(x))}{\mu_w} \quad (13)$$

Equation 14 provides a rearrangement of Equation 13 to solve for the water phase relative permeability ($K_{rw}$) as a function of location (x) along the longitudinal length (L) of the rock sample 101.

$$K_{rw}(x) = \frac{x\mu_w}{K} \frac{dV_w}{dP_w(x, V_w)} \qquad (14)$$

At step 202, a primary drainage process is conducted on the rock sample 101. In some implementations, the rock sample 101 is already saturated with water (or brine). In some implementations, the control valve 130a is closed, and the control valve 130b is open during the primary drainage process at step 202. The primary drainage process can include flowing a hydrocarbon stream into the first end 101a of the rock sample 101 at a first hydrocarbon flow rate. The hydrocarbon stream includes at least one hydrocarbon. The hydrocarbon stream can include, for example, crude oil or natural gas obtained from the same formation as the rock sample 101. In some implementations, the first hydrocarbon flow rate is in a range of from approximately 0.01 cc/min to approximately 10 cc/min. For example, the first hydrocarbon flow rate is approximately 0.5 cc/min, approximately 1 cc/min, approximately 2 cc/min, approximately 5 cc/min, approximately 8 cc/min, or approximately 10 cc/min. In some implementations, the first hydrocarbon flow rate is constant during the primary drainage process to ensure that the irreducible water saturation is reached at the first end 101a of the rock sample 101. For example, the first hydrocarbon flow rate can be approximately 10 cc/min for the primary drainage process. In some implementations, the first hydrocarbon flow rate varies during the primary drainage process. In some implementations, the first hydrocarbon flow rate can increase (for example, step-wise or gradually) during the primary drainage process. For example, the first hydrocarbon flow rate can be approximately 0.01 cc/min at the beginning of the primary drainage process, and the first hydrocarbon flow rate can be approximately 10 cc/min at the end of the primary drainage process. This increase to the final, largest flow rate (in this example, 10 cc/min) can ensure that the irreducible water saturation is reached at the first end 101a of the rock sample 101.

The primary drainage process can include flowing a water stream across the second end 101b of the rock sample 101 at a first water flow rate, while the hydrocarbon stream is flowed into the first end 101a of the rock sample 101 at the first hydrocarbon flow rate. As mentioned previously, the water stream includes a doping agent, such as potassium iodide, potassium bromide, or cesium chloride, so that the water stream is distinguishable from the hydrocarbon stream in the images captured by the imaging machine 154. The water stream can include additional components, such as a salt. For example, the water stream can include sodium chloride, potassium chloride, calcium chloride, magnesium chloride, sodium bicarbonate, sodium sulfate, or combinations of these. In some implementations, the first water flow rate is less than the first hydrocarbon flow rate. In some implementations, the first water flow rate is in a range of from approximately 0.1 cc/min to approximately 0.5 cc/min. For example, the first water flow rate can be approximately 0.3 cc/min. In some implementations, the first water flow rate is constant.

The flow of the hydrocarbon stream through the rock sample 101 and the flow of the water stream across the second end 101b of the rock sample 101 can result in a differential pressure across the longitudinal length of the rock sample 101. For example, the differential pressure resulting from the flows of the hydrocarbon stream and the water stream can be in a range of from approximately 1 pounds per square inch (psi) to 500 approximately psi. The flow of the hydrocarbon stream and the water stream to the rock sample 101 can continue until the flow across the rock sample 101 reaches a steady-state equilibrium condition—meaning the fluid saturation distribution monitored by the imaging machine 154 and the pressure distribution along a longitudinal length of the rock sample 101 stabilizes (that is, stops changing).

Once the flow across the rock sample 101 reaches the steady-state equilibrium condition for each of the different first hydrocarbon flow rates of the primary drainage process, the pressure distribution across the longitudinal length of the rock sample 101 is measured (and is also considered the capillary pressure distribution) by the various pressure sensors at step 214a, and the water saturation distribution across the longitudinal length of the rock sample 101 is measured by the imaging machine 154 at step 214b. In some implementations, the oil phase relative permeability ($K_{ro}$) can be calculated by Equation 5 or Equation 10 and can be combined with the measured water saturation distribution to yield an injected phase relative permeability curve for the different first hydrocarbon flow rates of the primary drainage process.

At step 204, a core aging process is conducted on the rock sample 101. The core aging process at step 204 is essentially a continuation of the primary drainage process at step 202. The core aging process can include continuing the flow of the hydrocarbon stream into the first end 101a of the rock sample 101 and the flow of the water stream across the second end 101b of the rock sample 101. The hydrocarbon stream exiting the second end 101b of the rock sample 101 as effluent can be recycled and flowed back into the first end 101a of the rock sample 101. Similarly, the water stream exiting the second end 101b of the rock sample 101 as effluent can be recycled and flowed back across the second end 101b of the rock sample 101. The core aging process at step 204 allows microscopic redistribution of hydrocarbon and water at the rock pore surface. In doing so, a fluid saturation and wettability distribution representative of an oil-water transition zone of a reservoir can be restored.

At step 206, a spontaneous water imbibition process is conducted on the rock sample 101. In some implementations, the control valve 130a is closed, and the control valve 130b is open during the spontaneous water imbibition process at step 206 (similar to steps 202 and 204). The spontaneous water imbibition process can include flowing the hydrocarbon stream into the first end 101a of the rock sample 101 at a second hydrocarbon flow rate. The spontaneous water imbibition process can include flowing the water stream across the second end 101b of the rock sample 101 at the first water flow rate (the same as in steps 202 and 204) while the hydrocarbon stream is flowed into the first end 101a of the rock sample 101. The second hydrocarbon flow rate at step 206 can be different from the first hydrocarbon flow rate of step 202. In some implementations, the second hydrocarbon flow rate is in a range of from approximately 0.01 cc/min to approximately 10 cc/min. The second hydrocarbon flow rate can vary during the spontaneous water imbibition process. In some implementations, the second hydrocarbon flow rate can decrease (for example, step-wise or gradually) during the spontaneous water imbibition process. For example, the second hydrocarbon flow rate can be approximately 10 cc/min at the beginning of the spontaneous water imbibition process, and the second hydrocarbon flow rate can be approximately 0.01 cc/min at the end of the spontaneous water imbibition process. For example, the second hydrocarbon flow rate can be 10 cc/min, then 8 cc/min, then 6 cc/min, then 4 cc/min, then 2 cc/min, then 1 cc/min, then 0.5 cc/min, then 0.4 cc/min, then 0.2 cc/min, then 0.1 cc/min, then 0.05 cc/min, and then 0.01 cc/min. For each of the different second hydrocarbon flow rates at step 206, the respective second hydrocarbon flow rate can be maintained until the flow across the rock sample 101 reaches a steady-state equilibrium condition. Once a steady-state equilibrium condition is reached, the second hydrocarbon flow rate can then be reduced to the next second hydrocarbon flow rate.

After flowing the hydrocarbon stream into the first end 101a of the rock sample 101 at the smallest of the second hydrocarbon flow rates (for example, 0.01 cc/min) and reaching the steady-state equilibrium condition, the control valve 130a can be opened, so that the hydrocarbon stream can flow across the first end 101a of the rock sample 101 while the water stream flows across the second end 101b of the rock sample 101 at the first water flow rate. This can allow for the capillary pressure to reach zero at each of the locations along the longitudinal length of the rock sample 101.

Each time the flow across the rock sample 101 reaches the steady-state equilibrium condition during step 206, the pressure distribution across the longitudinal length of the rock sample 101 is measured (and is also considered the capillary pressure distribution) by the various pressure sensors at step 214a, and the water saturation distribution across the longitudinal length of the rock sample 101 is measured by the imaging machine 154 at step 214b. In some implementations, the oil phase relative permeability ($K_{ro}$) at each location (x) along the longitudinal length (L) of the rock sample 101 can be calculated by Equation 5 or Equation 10 and can be combined with the measured water saturation distribution to yield an injected phase relative permeability curve for the different second hydrocarbon flow rates of the spontaneous water imbibition process.

At step 208, a forced water imbibition process is conducted on the rock sample 101. In some implementations, the control valve 130a is open, and the control valve 130b is closed during the forced water imbibition process at step 208. The forced water imbibition process can include flowing the water stream into the second end 101b of the rock sample 101 at a second water flow rate. The second water flow rate at step 208 can be different from the first water flow rate of steps 202, 204, and 206. In some implementations, the second water flow rate is in a range of from approximately 0.01 cc/min to approximately 10 cc/min. The second water flow rate can vary during the forced water imbibition process. In some implementations, the second water flow rate can increase (for example, step-wise or gradually) during the forced water imbibition process. For example, the second water flow rate can be approximately 0.01 cc/min at the beginning of the forced water imbibition process, and the second water flow rate can be approximately 10 cc/min at the end of the forced water imbibition process. For example, the second water flow rate can be 0.01 cc/min, then 0.05 cc/min, then 0.1 cc/min, then 0.2 cc/min, then 0.4 cc/min, then 0.5 cc/min, then 1 cc/min, then 2 cc/min, then 4 cc/min, then 6 cc/min, then 8 cc/min, and then 10 cc/min. For each of the different second water flow rates at step 208, the respective second water flow rate can be maintained until the flow across the rock sample 101 reaches a steady-state equilibrium condition. Once a steady-state equilibrium condition is reached, the second water flow rate can then be increased to the next second water flow rate. The forced water imbibition process can include flowing the hydrocarbon stream across the first end 101a of the rock sample 101 at a third hydrocarbon flow rate while the water stream is flowed into the second end 101b of the rock sample 101. In some implementations, the third hydrocarbon flow rate is in a range of from approximately 0.1 cc/min to approximately 0.5 cc/min. For example, the third hydrocarbon flow rate can be approximately 0.3 cc/min.

Each time the flow across the rock sample 101 reaches the steady-state equilibrium condition during step 208, the pressure distribution across the longitudinal length of the rock sample 101 is measured (and is also considered the capillary pressure distribution) by the various pressure sensors at step 214a, and the water saturation distribution across the longitudinal length of the rock sample 101 is measured by the imaging machine 154 at step 214b. In some implementations, the water phase relative permeability ($K_{rw}$) at each location (x) along the longitudinal length (L) of the rock sample 101 can be calculated by Equation 3 or Equation 14 and can be combined with the measured water saturation distribution to yield a forced water imbibition water phase relative permeability curve for the different second water flow rates of the forced water imbibition process.

At step 210, a spontaneous hydrocarbon imbibition process is conducted on the rock sample 101. The spontaneous hydrocarbon imbibition process can include flowing the water stream into the second end 101b of the rock sample 101 at a third water flow rate. The spontaneous hydrocarbon imbibition process can include flowing the hydrocarbon stream across the first end 101a of the rock sample 101 at the third hydrocarbon flow rate (the same as in step 208) while the water stream is flowed into the second end 101b of the rock sample 101. The third water flow rate at step 210 can be different from the second water flow rate of step 208. In some implementations, the third water flow rate at step 210 is the same as the second water flow rate of step 208 but in reverse order (from the largest flow rate to the smallest flow rate). In some implementations, the third water flow rate is in a range of from approximately 0.01 cc/min to approximately 10 cc/min. The third water flow rate can vary during the spontaneous hydrocarbon imbibition process. In some implementations, the third water flow rate can decrease (for example, step-wise or gradually) during the spontaneous hydrocarbon imbibition process. For example, the third water flow rate can be approximately 10 cc/min at the beginning of the spontaneous hydrocarbon imbibition process, and the third water flow rate can be approximately 0.01 cc/min at the end of the spontaneous hydrocarbon imbibition process. For example, the third water flow rate can be 10 cc/min, then 8 cc/min, then 6 cc/min, then 4 cc/min, then 2 cc/min, then 1 cc/min, then 0.5 cc/min, then 0.4 cc/min, then 0.2 cc/min, then 0.1 cc/min, then 0.05 cc/min, and then 0.01 cc/min. For each of the different third water flow rates at step 210, the respective third water flow rate can be maintained until the flow across the rock sample 101 reaches a steady-state equilibrium condition. Once a steady-state equilibrium condition is reached, the third water flow rate can then be reduced to the next third water flow rate.

After flowing the water stream into the second end 101b of the rock sample 101 at the smallest of the third water flow rates (for example, 0.01 cc/min) and reaching the steady-state equilibrium condition, the control valve 130b can be opened, so that the water stream flows across the second end 101b of the rock sample 101 while the hydrocarbon stream flows across the first end 101a of the rock sample 101 at the third hydrocarbon flow rate. This allows for the capillary pressure to reach zero at each of the locations along the longitudinal length of the rock sample 101.

Each time the flow across the rock sample 101 reaches the steady-state equilibrium condition during step 210, the pressure distribution across the longitudinal length of the rock sample 101 is measured (and is also considered the capillary pressure distribution) by the various pressure sensors at step 214a, and the water saturation distribution across the longitudinal length of the rock sample 101 is measured by the imaging machine 154 at step 214b. In some implementations, the water phase relative permeability ($K_{rw}$) at each location (x) along the longitudinal length (L) of the rock sample 101 can be calculated by Equation 3 or Equation 14 and can be combined with the measured water saturation distribution to yield a spontaneous hydrocarbon imbibition water phase relative permeability curve for the different third water flow rates of the spontaneous hydrocarbon imbibition process.

At step 212, a secondary drainage process is conducted on the rock sample 101. In some implementations, the control valve 130a is closed, and the control valve 130b is open during the secondary drainage process at step 212. The secondary drainage process can include flowing the hydrocarbon stream into the first end 101a of the rock sample 101 at a fourth hydrocarbon flow rate. The secondary drainage process can include flowing the water stream across the second end 101b of the rock sample 101 at the first water flow rate (the same as in steps 202, 204, and 206) while the hydrocarbon stream is flowed into the first end 101a of the rock sample 101. In some implementations, the fourth hydrocarbon flow rate is in a range of from approximately 0.01 cc/min to approximately 10 cc/min. The fourth hydrocarbon flow rate can vary during the second drainage process. In some implementations, the fourth hydrocarbon flow rate can increase (for example, step-wise or gradually) during the secondary drainage process. For example, the fourth hydrocarbon flow rate can be approximately 0.01 cc/min at the beginning of the secondary drainage process, and the fourth hydrocarbon flow rate can be approximately 10 cc/min at the end of the secondary drainage process. For example, the fourth hydrocarbon flow rate can be 0.01 cc/min, then 0.05 cc/min, then 0.1 cc/min, then 0.2 cc/min, then 0.4 cc/min, then 0.5 cc/min, then 1 cc/min, then 2 cc/min, then 4 cc/min, then 6 cc/min, then 8 cc/min, and then 10 cc/min. For each of the different fourth hydrocarbon flow rates at step 214, the respective fourth hydrocarbon flow rate can be maintained until the flow across the rock sample 101 reaches a steady-state equilibrium condition. Once a steady-state equilibrium condition is reached, the fourth hydrocarbon flow rate can then be increased to the next fourth hydrocarbon flow rate.

Each time the flow across the rock sample 101 reaches the steady-state equilibrium condition during step 212, the pressure distribution across the longitudinal length of the rock sample 101 is measured (and is also considered the capillary pressure distribution) by the various pressure sensors at step 214a, and the water saturation distribution across the longitudinal length of the rock sample 101 is measured by the imaging machine 154 at step 214b. In some implementations, the oil phase relative permeability ($K_{ro}$) at each location (x) along the longitudinal length (L) of the rock sample 101 can be calculated by Equation 5 or Equation 10 and can be combined with the measured water saturation distribution to yield a secondary drainage oil phase relative permeability curve for the different fourth hydrocarbon flow rates of the secondary drainage process.

After the secondary drainage process at step 212, a core cleaning process can be conducted on the rock sample 101. The core cleaning process can include flowing toluene through the rock sample 101. Toluene can be flowed through the rock sample at a flow rate in a range of approximately 0.1 cc/min to approximately 10 cc/min. In some implementations, toluene is flowed through the rock sample 101 for at least one hour. In some implementations, at least 5 pore volumes of toluene is flowed through the rock sample 101. The core cleaning process can include flowing methanol through the rock sample 101. Methanol can be flowed through the rock sample at a flow rate in a range of approximately 0.1 cc/min to approximately 10 cc/min. In some implementations, methanol is flowed to the rock sample 101 for at least one hour. In some implementations, at least 5 pore volumes of methanol is flowed through the rock sample 101. The core cleaning process can include alternating between flowing toluene and flowing methanol through the rock sample 101 until the effluent from the rock sample 101 becomes visually clear. Once the effluent from the rock sample 101 is visually clear, if the last fluid injection into the rock sample 101 was methanol, another injection of toluene can be provided to the rock sample 101.

After the core cleaning process, a hydrocarbon saturation process and a calibration process for the imaging machine 154 can be conducted. The hydrocarbon saturation process can include flowing the hydrocarbon stream through the rock sample 101 until the rock sample 101 is saturated with hydrocarbon (that is, 100% hydrocarbon saturation). The hydrocarbon stream can be flowed through the rock sample 101 at a flow rate in a range of approximately 0.1 cc/min to approximately 7 cc/min. The imaging machine 154 can be calibrated with the rock sample 101 at 100% hydrocarbon saturation. For example, the imaging machine 154 can be an x-ray imaging machine, and the x-ray imaging machine 154 can be calibrated with the rock sample 101 at 100% hydrocarbon saturation at reservoir conditions.

At step 216, for each of the locations (x) along the longitudinal length (L) of the rock sample 101 and for each of the different flow rates, the measured pressure distributions can be combined with the respective measured fluid saturation distribution to produce capillary pressure bounding curves and scanning loops for the rock sample 101 at the respective location (x). Similarly, for each of the locations (x) along the longitudinal length (L) of the rock sample 101 and for the different flow rates, the calculated relative permeability can be combined with the respective measured fluid saturation distribution to produce relative permeability bounding curves and scanning loops for the rock sample 101 at the respective location (x).

Example

FIGS. 3A, 3B, 3C, and 3D are various plots for an example rock sample 101. The sample was obtained from a subterranean formation of an oil reservoir. The sample had a cylindrical shape with a diameter of 3.8 centimeters and a length of 9 centimeters. The crude oil used in this example was also obtained from the same formation as the sample. The brine used in this example had a composition that included 8% cesium chloride and 1% potassium chloride by weight. 10 pressure transducers were evenly distributed along the length of the sample.

Figure 3A:
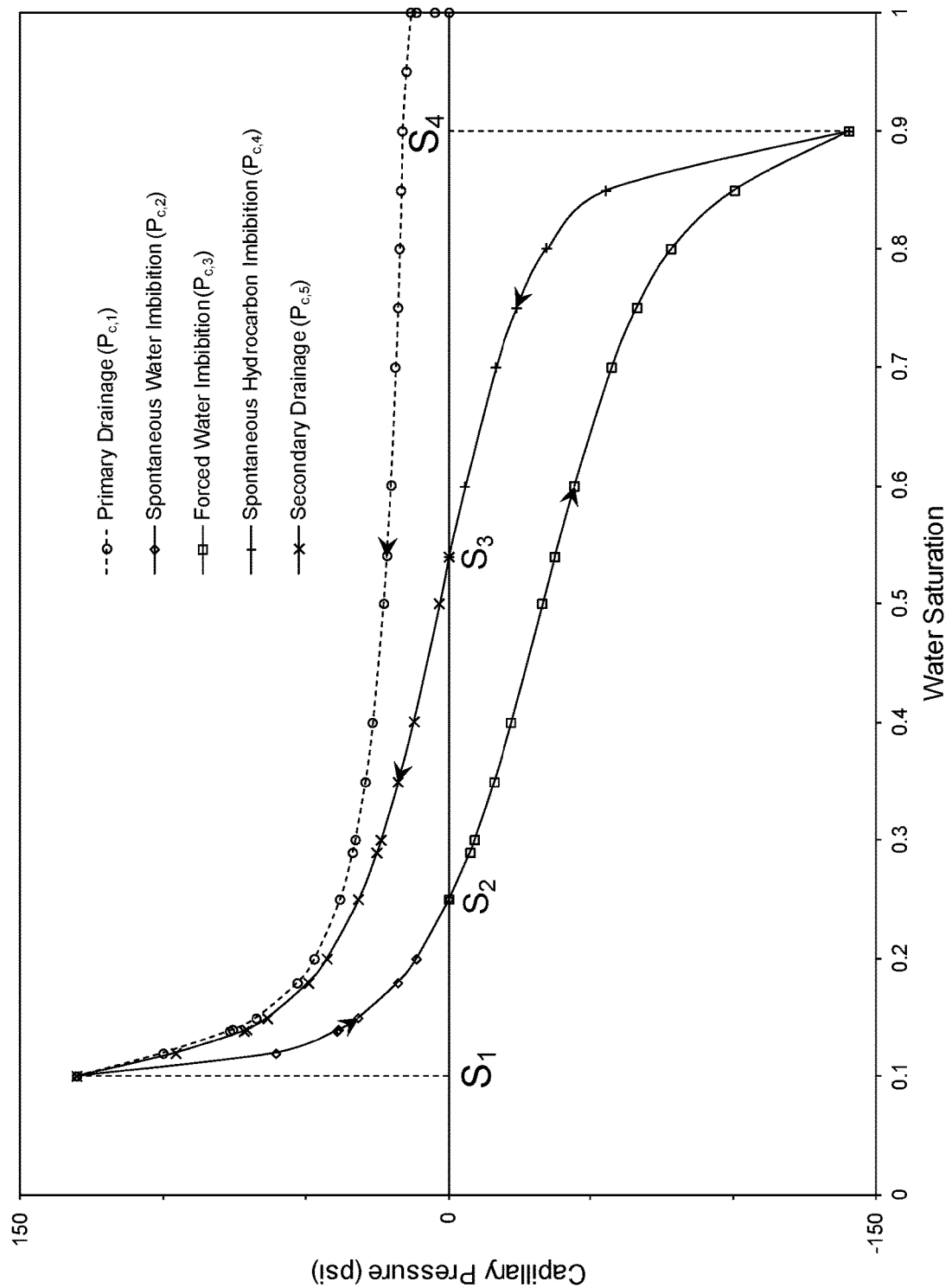
FIGS. 3A, 3B, 3C, and 3D are example plots for capillary pressure and relative permeability bounding curves and scanning loops of the rock sample.

FIG. 3A is a plot of capillary pressure ($P_d$) bounding curves of the sample in this example. $S_1$ was the minimum water saturation (which is also referred as the irreducible water saturation, $S_{wir}$=0.1) of the primary drainage capillary pressure curve ($P_{c,1}$). $S_2$ was the water saturation of the spontaneous water imbibition capillary pressure curve ($P_{c,2}$) at zero capillary pressure ($P_c$=0). $S_3$ was the water saturation of the spontaneous hydrocarbon imbibition capillary pressure curve ($P_{c,4}$) at zero capillary pressure ($P_c$=0). $S_4$ was the maximum water saturation of the forced water imbibition capillary pressure curve ($P_{c,3}$). $P_{c,5}$ is the secondary drainage capillary pressure curve. The arrows on the curves indicate the directions of water saturation change.

Figure 3B:
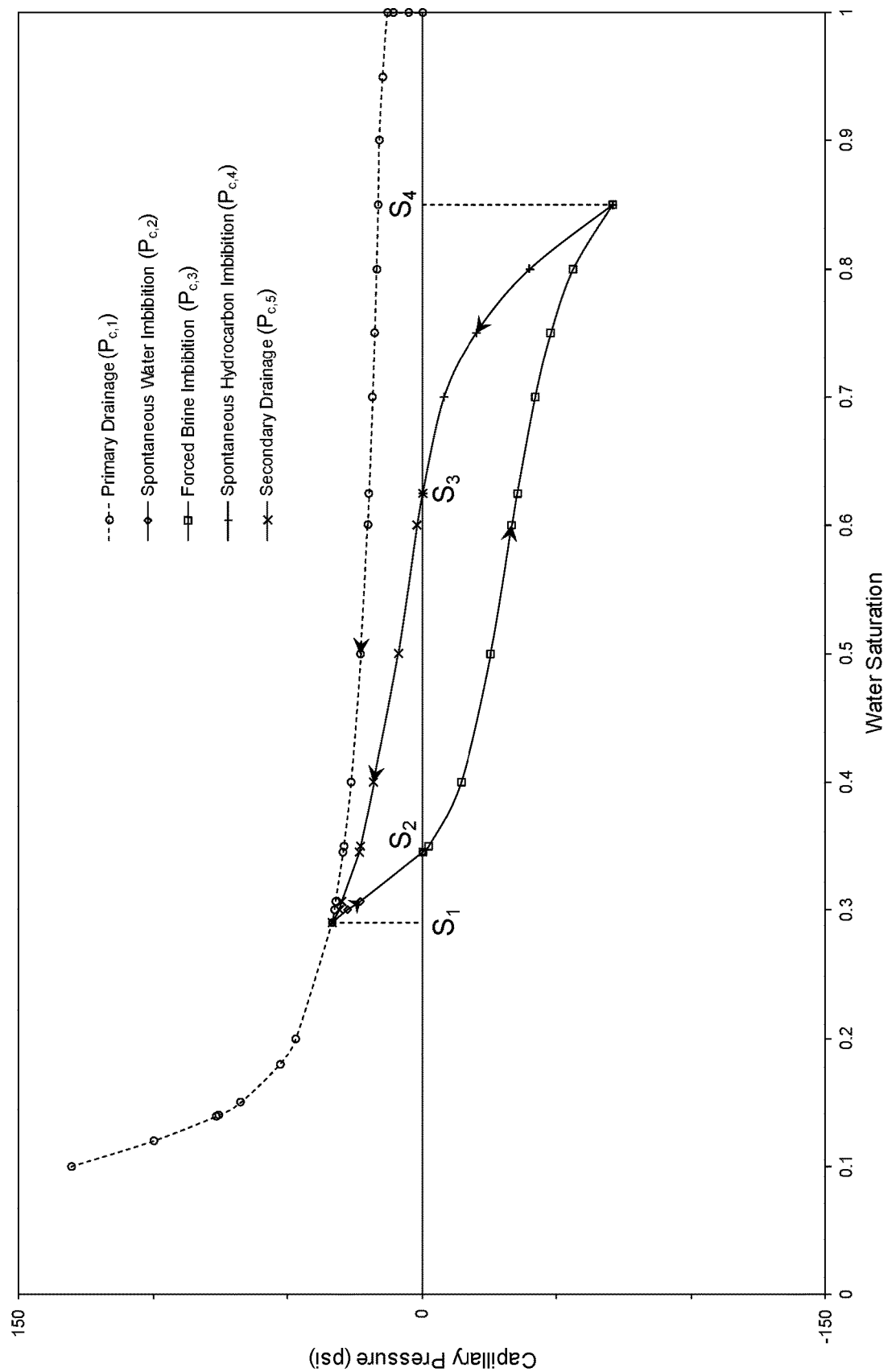

FIG. 3B is a plot of the primary drainage capillary pressure ($P_c$) bounding curve ($P_{c,1}$) and various capillary pressure ($P_c$) scanning curves ($P_{c,2}$, $P_{c,3}$, $P_{c,4}$, and $P_{c,5}$, yielding a scanning loop of capillary pressure ($P_c$) curves) at a location (x) of the sample in this example. $S_1$ was the initial water saturation ($S_{wi}$=0.29) of the scanning loop. $S_2$ was the water saturation of the spontaneous water imbibition capillary pressure curve ($P_{c,2}$) for zero capillary pressure ($P_c$=0). $S_3$ was the water saturation of the spontaneous hydrocarbon imbibition capillary pressure curve ($P_{c,4}$) at zero capillary pressure ($P_c$=0). $S_4$ was the maximum water saturation of the forced water imbibition capillary pressure curve ($P_{c,3}$). $P_{c,5}$ is the secondary drainage capillary pressure curve. The arrows on the curves indicate the directions of water saturation change.

Figure 3C:
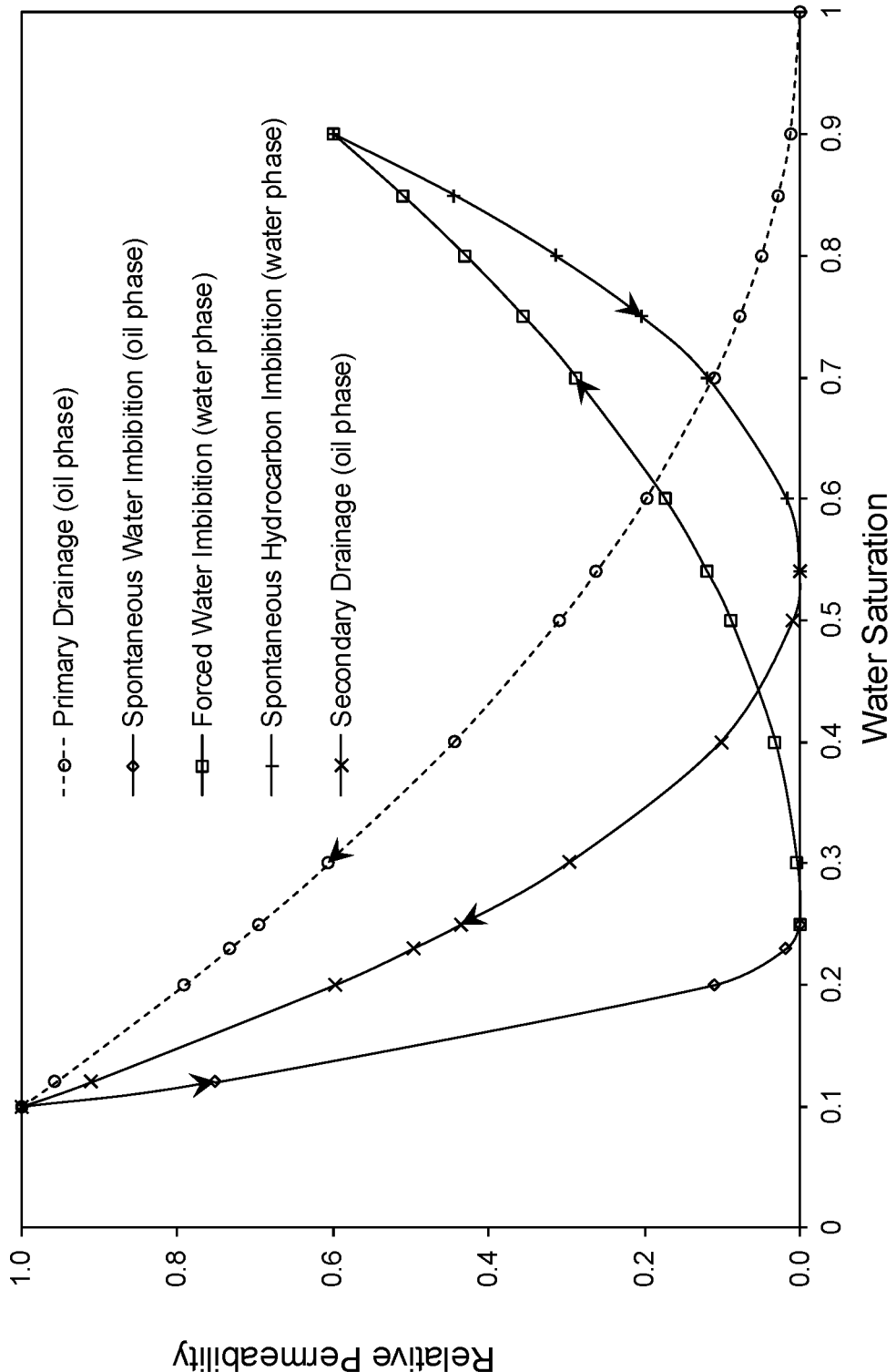

FIG. 3C is a plot of relative permeability ($K_r$) bounding curves of the sample in this example. The spontaneous water imbibition process started with an irreducible water saturation ($S_{wir}$=0.1). The arrows on the curves indicate the directions of water saturation change.

Figure 3D:
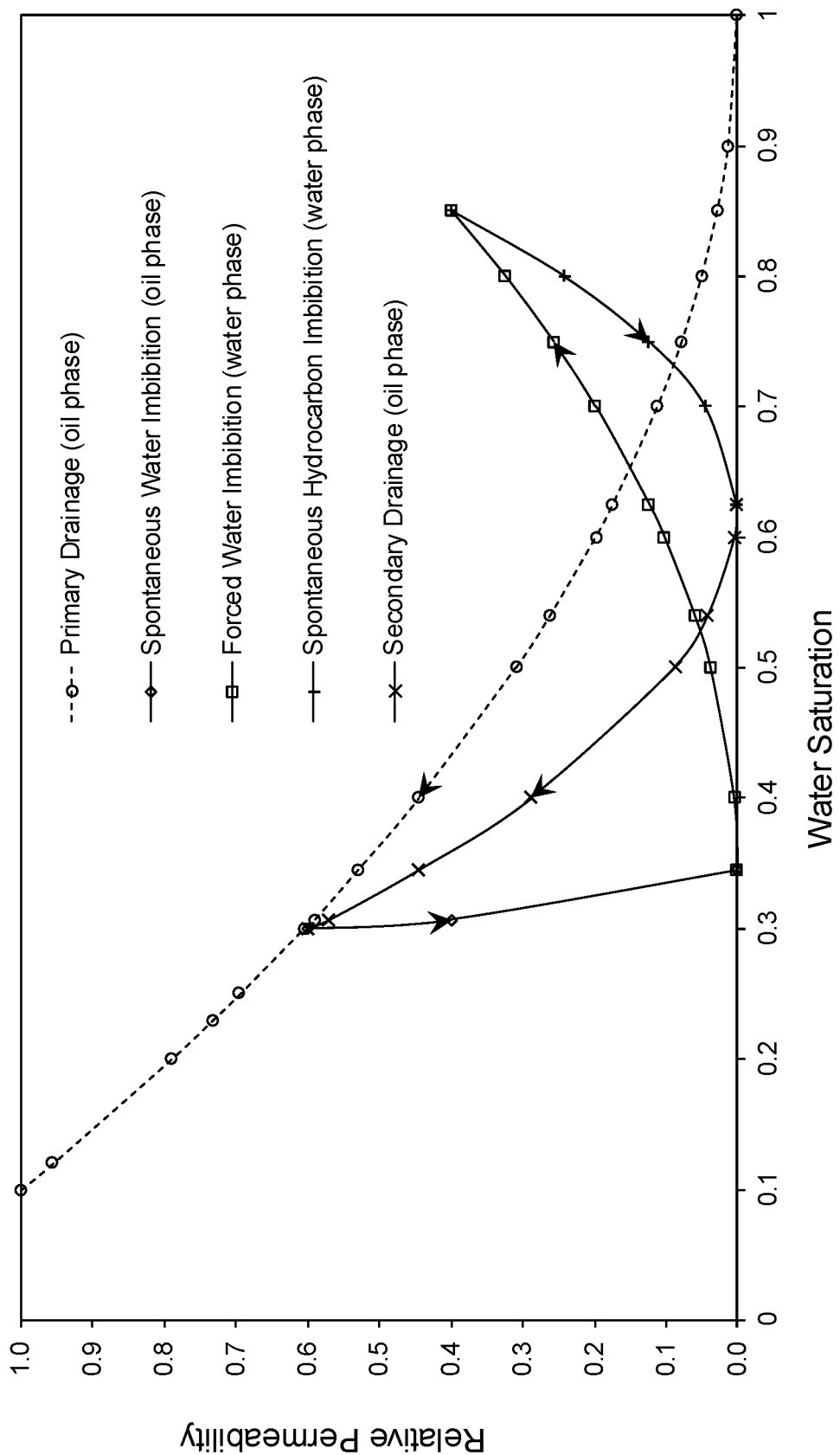

FIG. 3D is a plot of a primary drainage relative permeability ($K_r$) bounding curve and various relative permeability ($K_r$) scanning curves (which yield a scanning loop of relative permeability ($K_r$) curves) at location x of the sample in this example. The scanning loop started with an initial water saturation ($S_{wi}$=0.29) at location x. The arrows on the curves indicate the directions of water saturation change.

The various curves in each of FIGS. 3A, 3B, 3C, and 3D are attributable to the primary drainage process (step 202), the spontaneous water imbibition process (step 206), the forced water imbibition process (step 208), the spontaneous hydrocarbon imbibition process (step 210), and the secondary drainage process (step 212).

At step 218, a wettability index distribution along the longitudinal length (L) of the rock sample 101 is determined based on the capillary pressure bounding curves and scanning loops produced at step 216. The wettability can be calculated according to any known wettability index, for example, the Amott wettability index, the Amott-Harvey wettability index, or the United States Bureau of Mines (USBM) wettability index.

The Amott wettability index to water ($I_w(x)$) can be calculated by Equation 15:

$$I_w(x) = \frac{S_2 - S_1}{S_4 - S_1} \quad (15)$$

The Amott wettability index to oil ($I_o(x)$) can be calculated by Equation 16:

$$I_o(x) = \frac{S_4 - S_3}{S_4 - S_1} \quad (16)$$

The Amott-Harvey wettability index ($I_{AH}(x)$) can be calculated by Equation 17:

$$I_{AH}(x) = \frac{S_2 + S_3 - S_1 - S_4}{S_4 - S_1} \quad (17)$$

The USBM wettability index ($I_{USBM}(x)$) can be calculated by Equation 18:

$$I_{USBM}(x) = \log\left(\frac{\int_{S_1}^{S_3} P_{c,5}(S_w)dS_w}{\int_{S_2}^{S_4} P_{c,3}(S_w)dS_w}\right) \quad (18)$$

where $P_{c,3}(S_w)$ is the forced water imbibition capillary pressure as a function of water saturation ($S_w$), and $P_{c,5}(S_w)$ is the secondary drainage capillary pressure as a function of water saturation ($S_w$), as shown in FIGS. 3A and 3B.

A correlation between initial hydrocarbon saturation ($S_{oi}$) and residual hydrocarbon saturation ($S_{or}$) can be determined. The correlation can be determined from the same data set obtained on the sample. The correlation can be useful for reservoir evaluation, especially for the oil-water transition zone. The correlation can be determined using Equation 19 and Equation 20.

$$S_{oi} = 1 - S_1 \quad (19)$$

$$S_{or} = 1 - S_4 \quad (20)$$

Figure 4:
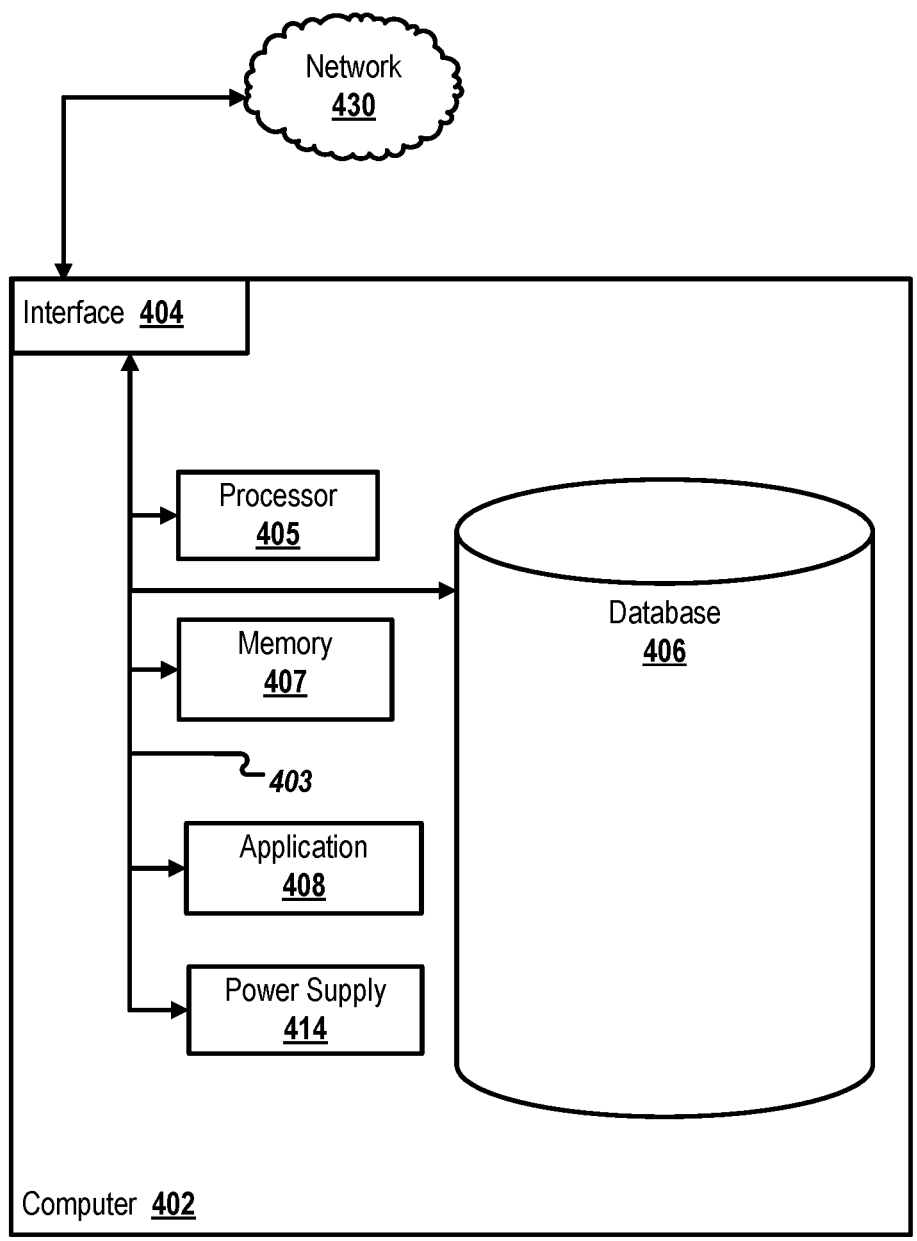
FIG. 4 is a block diagram illustrating an example computer system that can be used to provide computational functionalities associated with described algorithms, methods, functions, processes, flows, and procedures as described in the present disclosure.

FIG. 4 is a block diagram of an example computer system 400 that can be used to provide computational functionalities associated with described algorithms, methods, functions, processes, flows, and procedures described in the present disclosure, according to some implementations of the present disclosure. For example, the computer system 400 can be used to automate method 200. For example, the computer system 400 can be used to perform the calculations associated with Equations 1-20. For example, the computer system 400 can be used to store the calculated values. The illustrated computer 402 is intended to encompass any computing device such as a server, a desktop computer, a laptop/notebook computer, a wireless data port, a tablet computing device, or one or more processors within these devices, including physical instances, virtual instances, or both. The computer 402 can include input devices such as keypads, keyboards, and touch screens that can accept user information. Also, the computer 402 can include output devices that can convey information associated with the operation of the computer 402. The information can include digital data, visual data, audio information, or a combination of information. The information can be presented in a graphical user interface (UI) (or GUI).

The computer 402 can serve in a role as a client, a network component, a server, a database, a persistency, or components of a computer system for performing the subject matter described in the present disclosure. The illustrated computer 402 is communicably coupled with a network 430. In some implementations, one or more components of the computer 402 can be configured to operate within different environments, including cloud-computing-based environments, local environments, global environments, and combinations of environments.

At a high level, the computer 402 is an electronic computing device operable to receive, transmit, process, store, and manage data and information associated with the described subject matter. According to some implementations, the computer 402 can also include, or be communicably coupled with, an application server, an email server, a web server, a caching server, a streaming data server, or a combination of servers.

The computer 402 can receive requests over network 430 from a client application (for example, executing on another computer 402). The computer 402 can respond to the received requests by processing the received requests using software applications. Requests can also be sent to the computer 402 from internal users (for example, from a command console), external (or third) parties, automated applications, entities, individuals, systems, and computers.

Each of the components of the computer 402 can communicate using a system bus 403. In some implementations, any or all of the components of the computer 402, including hardware or software components, can interface with each other or the interface 404 (or a combination of both), over the system bus 403. Interfaces can use an application programming interface (API), a service layer, or a combination of the API and service layer.

The computer 402 includes an interface 404. Although illustrated as a single interface 404 in FIG. 4, two or more interfaces 404 can be used according to particular needs, desires, or particular implementations of the computer 402 and the described functionality. The interface 404 can be used by the computer 402 for communicating with other systems that are connected to the network 430 (whether illustrated or not) in a distributed environment. Generally, the interface 404 can include, or be implemented using, logic encoded in software or hardware (or a combination of software and hardware) operable to communicate with the network 430. More specifically, the interface 404 can include software supporting one or more communication protocols associated with communications. As such, the network 430 or the interface's hardware can be operable to communicate physical signals within and outside of the illustrated computer 402.

The computer 402 includes a processor 405. Although illustrated as a single processor 405 in FIG. 4, two or more processors 405 can be used according to particular needs, desires, or particular implementations of the computer 402 and the described functionality. Generally, the processor 405 can execute instructions and can manipulate data to perform the operations of the computer 402, including operations using algorithms, methods, functions, processes, flows, and procedures as described in the present disclosure.

The computer 402 can include a database 406 that can hold data for the computer 402 and other components connected to the network 430 (whether illustrated or not). For example, database 406 can be an in-memory, conventional, or a database storing data consistent with the present disclosure. In some implementations, database 406 can be a combination of two or more different database types (for example, hybrid in-memory and conventional databases) according to particular needs, desires, or particular implementations of the computer 402 and the described functionality. Although illustrated as a single database 406 in FIG. 4, two or more databases (of the same, different, or combination of types) can be used according to particular needs, desires, or particular implementations of the computer 402 and the described functionality. While database 406 is illustrated as an internal component of the computer 402, in alternative implementations, database 406 can be external to the computer 402.

The computer 402 includes a memory 407 that can hold data for the computer 402 or a combination of components connected to the network 430 (whether illustrated or not). Memory 407 can store any data consistent with the present disclosure. In some implementations, memory 407 can be a combination of two or more different types of memory (for example, a combination of semiconductor and magnetic storage) according to particular needs, desires, or particular implementations of the computer 402 and the described functionality. Although illustrated as a single memory 407 in FIG. 4, two or more memories 407 (of the same, different, or combination of types) can be used according to particular needs, desires, or particular implementations of the computer 402 and the described functionality. While memory 407 is illustrated as an internal component of the computer 402, in alternative implementations, memory 407 can be external to the computer 402.

The application 408 can be an algorithmic software engine providing functionality according to particular needs, desires, or particular implementations of the computer 402 and the described functionality. For example, application 408 can serve as one or more components, modules, or applications. Further, although illustrated as a single application 408, the application 408 can be implemented as multiple applications 408 on the computer 402. In addition, although illustrated as internal to the computer 402, in alternative implementations, the application 408 can be external to the computer 402.

The computer 402 can also include a power supply 414. The power supply 414 can include a rechargeable or non-rechargeable battery that can be configured to be either user- or non-user-replaceable. In some implementations, the power supply 414 can include power-conversion and management circuits, including recharging, standby, and power management functionalities. In some implementations, the power-supply 414 can include a power plug to allow the computer 402 to be plugged into a wall socket or a power source to, for example, power the computer 402 or recharge a rechargeable battery.

There can be any number of computers 402 associated with, or external to, a computer system containing computer 402, with each computer 402 communicating over network 430. Further, the terms "client," "user," and other appropriate terminology can be used interchangeably, as appropriate, without departing from the scope of the present disclosure. Moreover, the present disclosure contemplates that many users can use one computer 402 and one user can use multiple computers 402.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

As used in this disclosure, the term "about" or "approximately" can allow for a degree of variability in a value or range, for example, within 10%, within 5%, or within 1% of a stated value or of a stated limit of a range.

As used in this disclosure, the term "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A method comprising:
   conducting a primary drainage process on a rock sample;
   conducting a core aging process on the rock sample;
   conducting a spontaneous water imbibition process on the rock sample;
   conducting a forced water imbibition process on the rock sample;
   conducting a spontaneous hydrocarbon imbibition process on the rock sample;
   conducting a secondary drainage process on the rock sample;
   for each of the primary drainage process, the spontaneous water imbibition process, the forced water imbibition process, the spontaneous hydrocarbon imbibition process, and the secondary drainage process:
      measuring a pressure distribution across a plurality of locations along a longitudinal length of the rock sample; and
      measuring a fluid saturation distribution across the plurality of locations along the longitudinal length of the rock sample;
   for each of the locations along the longitudinal length of the rock sample:
      combining the pressure distribution and the fluid saturation distribution to produce a capillary pressure bounding curve and scanning loop for the rock sample at the respective location; and
      determining a relative permeability bounding curve and scanning loop at least based on the measured fluid saturation distribution and pressure distribution at the respective location; and
   determining a wettability distribution along the longitudinal length of the rock sample based on the capillary pressure bounding curves and scanning loops.

2. The method of claim 1, further comprising:
   saturating the rock sample with a water stream;
   calibrating an imaging machine using the rock sample saturated with the water stream; and
   determining a permeability distribution across the plurality of locations along the longitudinal length of the rock sample based on the measured pressure distribution.

3. The method of claim 1, further comprising conducting a cleaning process on the rock sample, the cleaning process comprising:
   a) flowing toluene through the rock sample;
   b) flowing methanol through the rock sample; and
   c) repeating and alternating between steps a) and b) until an effluent from the rock sample is visually clear.

4. The method of claim 1, further comprising:
   saturating the rock sample with a hydrocarbon stream; and
   calibrating an imaging machine using the rock sample saturated with the hydrocarbon stream.

5. The method of claim 1, further comprising determining a correlation between an initial hydrocarbon saturation and a residual hydrocarbon saturation based on the measured fluid saturation distributions across the plurality of locations along the longitudinal length of the rock sample.

6. The method of claim 1, further comprising, for each of the locations (x) along the longitudinal length of the rock sample, determining a relative permeability of a water phase ($K_{rw}$) to be:

$$K_{rw}(x) = -\frac{V_w \mu_w}{K}\left(\frac{dP_w(x)}{dx}\right)^{-1},$$

wherein K is absolute permeability, $V_w$ is velocity of the water phase flowing through the rock sample, $\mu_w$ is dynamic viscosity of the water phase, $dP_w(w)$ is pressure drop of the water phase, and dx is length over which the pressure drop is taking place.

7. The method of claim 6, further comprising, for each of the locations (x) along the longitudinal length of the rock sample, determining the relative permeability of the water phase ($K_{rw}$) to be:

$$K_{rw}(x) = \frac{x \mu_w}{K}\frac{dV_w}{dP_w(x, V_w)}.$$

8. The method of claim 1, further comprising, for each of the locations (x) along the longitudinal length of the rock sample, determining a relative permeability of a hydrocarbon phase ($K_{ro}$) to be:

$$K_{ro}(x) = -\frac{V_o \mu_o}{K}\left(\frac{dP_o(x)}{dx}\right)^{-1},$$

wherein K is absolute permeability, $V_o$ is velocity of the hydrocarbon phase flowing through the rock sample, $\mu_o$ is dynamic viscosity of the hydrocarbon phase, $dP_o(x)$ is pressure drop of the hydrocarbon phase, and dx is length over which the pressure drop is taking place.

9. The method of claim 8, further comprising, for each of the locations (x) along the longitudinal length (L) of the rock sample, determining the relative permeability of the hydrocarbon phase ($K_{ro}$) to be:

$$K_{ro}(x) = \frac{(L-x)\mu_o}{K} \frac{dV_o}{dP_o(x, V_o)}.$$

10. The method of claim 1, wherein each of the primary drainage process and the core aging process comprises:
flowing a hydrocarbon stream into a first end of the rock sample at a first hydrocarbon flow rate; and
while flowing the hydrocarbon stream, flowing a water stream across a second end of the rock sample at a first water flow rate.

11. The method of claim 10, wherein the spontaneous water imbibition process comprises:
flowing the water stream across the second end of the rock sample at the first water flow rate; and
while flowing the water stream, flowing the hydrocarbon stream into the first end of the rock sample at a second hydrocarbon flow rate.

12. The method of claim 11, wherein the spontaneous water imbibition process further comprises, while flowing the water stream and after flowing the hydrocarbon stream at the second hydrocarbon flow rate, decreasing the flow of the hydrocarbon stream into the first end of the rock sample.

13. The method of claim 12, wherein the spontaneous water imbibition process further comprises, while flowing the water stream, flowing the hydrocarbon stream across the first end of the rock sample.

14. The method of claim 11, wherein the forced water imbibition process comprises:
flowing the hydrocarbon stream across the first end of the rock sample at a third hydrocarbon flow rate; and
while flowing the hydrocarbon stream, flowing the water stream into the second end of the rock sample at a second water flow rate.

15. The method of claim 14, wherein the forced water imbibition process further comprises, while flowing the hydrocarbon stream and after flowing the water stream at the second water flow rate, increasing the flow of the water stream into the second end of the rock sample.

16. The method of claim 14, wherein the secondary drainage process comprises:
flowing the water stream across the second end of the rock sample at the first water flow rate; and
while flowing the water stream, flowing the hydrocarbon stream into the first end of the rock sample at a fourth hydrocarbon flow rate.

17. The method of claim 14, wherein the spontaneous hydrocarbon imbibition process comprises:
flowing the hydrocarbon stream across the first end of the rock sample at the third hydrocarbon flow rate; and
while flowing the hydrocarbon stream, flowing the water stream into the second end of the rock sample at a third water flow rate.

18. The method of claim 17, wherein the spontaneous hydrocarbon imbibition process further comprises, while flowing the hydrocarbon stream and after flowing the water stream at the third water flow rate, decreasing the flow of the water stream into the second end of the rock sample.

19. The method of claim 18, wherein the spontaneous hydrocarbon imbibition process further comprises, while flowing the hydrocarbon stream, flowing the water stream across the second end of the rock sample.

20. The method of claim 18, wherein the secondary drainage process further comprises, while flowing the water stream and after flowing the hydrocarbon stream at the fourth hydrocarbon flow rate, increasing the flow of the hydrocarbon stream into the first end of the rock sample.

* * * * *